(12) United States Patent
Ivri

(10) Patent No.: US 6,629,646 B1
(45) Date of Patent: *Oct. 7, 2003

(54) DROPLET EJECTOR WITH OSCILLATING TAPERED APERTURE

(75) Inventor: Yehuda Ivri, Irvine, CA (US)

(73) Assignee: Aerogen, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/163,850

(22) Filed: Dec. 7, 1993

Related U.S. Application Data

(63) Continuation-in-part of application No. 07/726,777, filed on Jul. 8, 1991, now abandoned, which is a continuation-in-part of application No. 07/691,584, filed on Apr. 24, 1991, now Pat. No. 5,164,740.

(51) Int. Cl.[7] ............................................... B05B 17/04
(52) U.S. Cl. ........................... 239/4; 239/102.2; 347/47
(58) Field of Search ........................... 239/4, 102.2, 110, 239/120, 121, 122; 347/47, 54, 20, 68; 222/196

(56) References Cited

U.S. PATENT DOCUMENTS

| 2,779,623 A | 1/1957 | Eisenkraft |
| 3,558,052 A | 1/1971 | Dunn |

(List continued on next page.)

FOREIGN PATENT DOCUMENTS

| EP | 0049636 | 4/1982 |
| EP | 0103161 | 3/1984 |
| EP | 0134847 | 3/1985 |
| EP | 542723 A2 | 12/1990 |
| GB | 973458 | 10/1962 |
| GB | 1454597 | 11/1976 |
| GB | 2073616 | 4/1981 |
| GB | 2177623 A | 1/1987 |
| GB | 2240494 | 12/1990 |
| JP | 57-23852 | 2/1982 |
| JP | 57-105608 | 7/1982 |
| JP | 58-61857 | 4/1983 |
| JP | 604174 | 1/1985 |
| JP | 60-4714 | 1/1985 |
| JP | 618357 | 1/1986 |
| JP | 61215059 | 9/1986 |
| JP | 2-135169 | 5/1990 |
| JP | 2-189161 | 7/1990 |
| WO | 9211050 | 12/1991 |
| WO | 9301404 | 6/1992 |

OTHER PUBLICATIONS

Review of Scientific Instruments, 57 (11), Nov. 1986, pp. 2870–2876, by Maehara et al.

(List continued on next page.)

Primary Examiner—Steven J. Ganey
(74) Attorney, Agent, or Firm—Townsend and Townsend and Crew LLP

(57) ABSTRACT

A fluid injection device for ejecting fluid droplets in response to electrical signals comprises an oscillating surface that has one or more tapered apertures, each aperture having a first and second opening. The first opening of each aperture is larger than the second opening. The first opening is in surface tension contact with the fluid to be ejected. The fluid interaction with the tapered aperture wall creates cycles of fluid compression and decompression inside the aperture, causing fluid to be drawn from the large opening and ejected out the small opening of the aperture. The device includes a fluid supply nozzle that transports fluid to the oscillating surface at the large opening of the apertures. A discharge valve controls the fluid supply. An electronic wave generator induces oscillation in the tapered aperture containing surface. The device is used to great advantage for fluid atomization and fluid spray.

29 Claims, 6 Drawing Sheets

U.S. PATENT DOCUMENTS

| | | |
|---|---|---|
| 3,738,574 A | 6/1973 | Guntersdorfer et al. |
| 3,790,079 A | 2/1974 | Berglund et al. |
| 3,804,329 A | 4/1974 | Martner |
| 3,812,854 A | 5/1974 | Michaels et al. |
| 3,950,760 A | 4/1976 | Rauch et al. |
| 3,958,249 A | 5/1976 | DeMaine et al. |
| 3,983,740 A | 10/1976 | Danel |
| 4,005,435 A | 1/1977 | Lundquist et al. |
| 4,159,803 A | 7/1979 | Cameto et al. |
| 4,240,081 A | 12/1980 | Devitt |
| 4,261,512 A | 4/1981 | Zierenberg |
| 4,294,407 A | 10/1981 | Reichl et al. |
| 4,300,546 A | 11/1981 | Kruber |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,389,071 A | 6/1983 | Johnson, Jr. et al. |
| 4,408,719 A | 10/1983 | Last |
| 4,431,136 A | 2/1984 | Janner et al. |
| 4,465,234 A | 8/1984 | Maehara et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,530,464 A | 7/1985 | Yamamoto et al. |
| 4,533,082 A | 8/1985 | Maehara et al. |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,591,883 A | 5/1986 | Isayama |
| 4,593,291 A | 6/1986 | Howkins |
| 4,605,167 A | 8/1986 | Maehara |
| 4,620,201 A | 10/1986 | Heinzl et al. |
| 4,628,890 A | 12/1986 | Freeman |
| 4,632,311 A | 12/1986 | Nakane et al. |
| 4,659,014 A | 4/1987 | Soth et al. |
| 4,681,264 A | 7/1987 | Johnson, Jr. |
| 4,702,418 A | 10/1987 | Carter et al. |
| 4,753,579 A | 6/1988 | Murphy |
| 4,790,479 A | 12/1988 | Matsumoto et al. |
| 4,796,807 A | 1/1989 | Bendig et al. |
| 4,799,622 A | 1/1989 | Ishikawa et al. |
| 4,828,886 A | 5/1989 | Hieber |
| 4,850,534 A | 7/1989 | Takahashi et al. |
| 4,865,006 A | 9/1989 | Nogi et al. |
| 4,888,516 A | 12/1989 | Daeges et al. |
| 5,021,701 A | 6/1991 | Takahashi et al. |
| 5,063,396 A | 11/1991 | Shiokawa et al. |
| 5,152,456 A | 10/1992 | Ross et al. |
| 5,164,740 A | 11/1992 | Ivri |
| 5,198,157 A | 3/1993 | Bechet |
| 5,261,601 A * | 11/1993 | Ross et al. |
| 5,297,734 A | 3/1994 | Toda |
| 5,299,739 A | 4/1994 | Takahashi et al. |

OTHER PUBLICATIONS

Siemens AG, 1989, "Ink–Jet Printing: The Present State of the Art," by Wolfgang R. Wehl.

Berglund, R.N., et al. Generation of Monodisperse Aerosol Standards. Environ. Sci. Technology 7:2:147 (1973).

Allen, T. Particle Size Measurement. Chapman and Hall pp. 167–169 (1981).

Ueha, S., et al. Mechanism of Ultrasonic Atomization Using a Multi–Pinhole Plate. J. Acoust. Soc. Jpn. (E)6,1:21 (1985).

Maehara, N., et al. Optimum Design Procedure for Multi–Pinhole–Plate Ultrasonic Atomizer. Japanese Journal of Applied Physics, 26:215 (1987).

Ashgriz, N., et al. Development of a Controlled Spray Generator. Rev. Sci. Instrum. 58(7):1291 (1987).

Hikayama, H., et al. Ultrasonic Atomizer with Pump Function. Tech. Rpt. IEICE Japan US88–74:25 (1988).

J. Acoustical Soc. Japan 44:2:116 (1988).

J. Acoustical Soc. Japan 44:6:425 (1988).

TSI Incorporated product catalog. Vibrating Orifice Aerosol Generator (1989).

Gaiser Tool Company catalog, pp. 26, 29–30 (1990).

Nogi, T., et al. Mixture Formation of Fuel Injection System in Gasoline Engine. Nippon Kikai Gakkai Zenkoku Taikai Koenkai Koen Ronbunshu 69:660 (1991).

* cited by examiner

DROPLET EJECTOR WITH OSCILLATING TAPERED APERTURE

CROSS-REFERENCE TO RELATED APPLICATIONS

This application is a continuation-in-part of patent application Ser. No. 07/726,777 filed on Jul. 8, 1991, now abandoned which is a continuation-in-part of patent application Ser. No. 07/691,584 filed on Apr. 24, 1991, now U.S. Pat. No. 5,164,740.

BACKGROUND OF THE INVENTION

1. Field of the Invention

The present invention relates to the fields of liquid spray and atomization of liquids of all kinds and, more specifically, finds utility in humidification and misting, industrial cleaning, surface coating and treatment, particle coating and encapsulating, fuel atomization, and medical spray applications.

2. Description of Related Art

Many types of ultrasonic fluid ejection devices have been developed for atomizing of water or liquid fuel. These atomizers can be classified into two groups. The first type atomizes liquid that forms a thin layer on an ultrasonically-excited plate. The first type is not capable of ejecting atomized fluid droplets. U.S. Pat. No. 3,738,574 describes an atomizer of this type.

The second type utilizes a housing defining an enclosed chamber. The housing includes a perforated membrane or a pinhole membrane as the front wall of the chamber. The apparatus further includes a means to vibrate the membrane or a side wall of the chamber, typically by a piezoelectric element affixed to the front face of the chamber. The piezoelectric element oscillates the fluid in the chamber. As a result, pressure waves are generated in the chamber, forcing fluid through the open pinholes. All the devices of the second type require fluid to be kept inside the chamber next to the discharge opening. When volatile fluids are used, problems arise. The volatile fluids escape through the discharge opening. The discharge opening will clog, restricting or stopping further discharge. These problems are prevalent with volatile fluids such as fuel, paint, or other coating materials. To overcome these problems, U.S. Pat. No. 4,632,311 utilizes a chamber with a suction pump in communication with the chamber. The pump is energized after operation to drain the liquid from the chamber, leaving it dry during nonworking periods. This is supposed to prevent otherwise solid substances from clogging the nozzle opening. U.S. Pat. No. 4,533,082 uses a vacuum pump to ensure that the liquid in the chamber is kept under negative pressure during nonuse. In these devices it is particularly difficult to feed fluid into the chamber without causing the fluid to uncontrollably flow out of the discharge opening.

Other variations of apparatus for ejecting atomized liquid, utilizing one of the above two types, are disclosed in U.S. Pat. Nos. 3,812,854, 4,159,803, 4,300,546, 4,334,531, 4,465,234, 4,632,311, 4,338,576, and 4,850,534.

SUMMARY OF THE INVENTION

The present invention provides an ejection device that includes a free oscillating surface having microscopic tapered apertures of a selected conical cross-sectional shape. The apertures draw fluid into their large openings and eject the fluid from their small openings to a great distance. The ejection action is developed by the aperture, regardless of the amount of fluid in contact with the oscillating surface, and without any fluid pressure. Both sides of the oscillating surface are operating under the same ambient pressure. Therefore, the ejection device can operate equally well in vacuum or high-pressure environments. When only a thin film of fluid is allowed to adhere, in surface tension contact, to the large opening of an aperture, the supplied liquid continuously adheres to the large opening by surface tension. The film of fluid oscillates with the surface while it is being drawn into the large opening of the aperture and ejected forwardly. This continues until all the fluid is drawn from the surface, leaving the surface dry and free of liquid during the time that the device is not in use.

If the cross-section of the aperture is chosen with respect to the fluid to be ejected, the oscillation required to produce ejection is kept small, and the film of fluid on the oscillating surface appears to be dynamically at rest during ejection. By supplying only enough fluid to continuously form a thin film, in surface tension contact with the oscillating surface, to the side containing the large openings of the tapered apertures, neither clogging nor uncontrolled emission or leakage through the apertures occurs. The device can operate under any pressure conditions.

BRIEF DESCRIPTION OF THE DRAWINGS

The general purpose and advances of the present invention will be more fully understood hereinafter as a result of the detailed description of the preferred embodiments when taken in conjunction with the following drawings, in which.

INTRODUCTION

Figure 1:
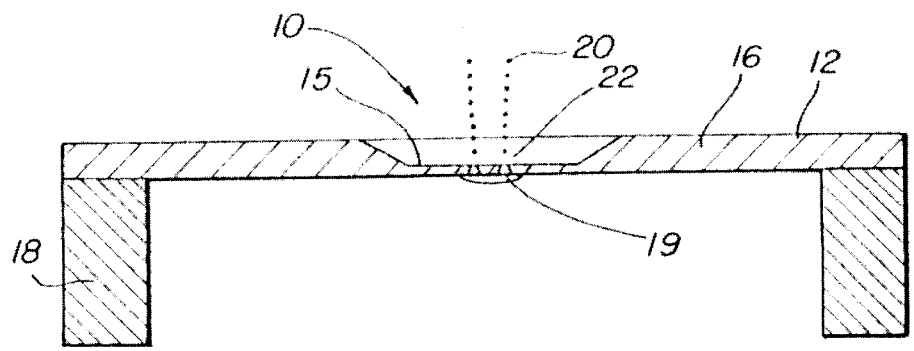
FIG. 1 is a schematic illustration of a preferred embodiment of a device according to the present invention.

The present invention provides a new fluid ejection device that is especially advantageous in applications that require ejection of fluid droplets without fluid pressure and without a propellant and in ambient pressure environments.

A particularly important application for the present invention is industrial spray systems. The ejector is capable of ejecting viscose liquid such as paint and coating materials without the use of compressed air.

The use of air as a propellant in paint spray application causes overspray, in that part of the paint droplets escape to the atmosphere and cause air pollution. The transfer efficiency, that is, the percentage amount of coating material, such as paint, that reaches the target, is significantly increased when ejection is without air.

Another important application of the present invention is for consumer products such as deodorant and hair spray. The use of propellants in conventional aerosols, commonly known as volatile organic chemicals (VOCs), has a negative effect on the environment and on human health. There is an ongoing trend to find ways to atomize fluid without using such propellant gases.

The present invention provides a device that ejects fluid from microscopic tapered apertures. The fluid is transported to the ejecting surface at the large opening of the tapered aperture. A cohesive attraction force (surface tension) exclusively causes the liquid to adhere to the tapered aperture. The solid/fluid interaction of the fluid with the tapered aperture wall causes fluid to be drawn into the large opening of the aperture and ejected from its small opening. This ejection action is attributed to the geometry of the aperture, as well as the fluid characteristics such as viscosity, density, and elasticity. The fluid supply to the surface is tightly controlled to prevent overflow of liquid from the supply side of the oscillating surface. A flow control valve or a two-way valve is provided to control the amount of fluid that is transported to the surface. The valve may have a built-in electrical contact that activates oscillation simultaneously with the flow of fluid.

During ejection, fluid is supplied to the oscillating surface from a discharge nozzle that is in close proximity to the oscillating surface. The fluid is held by surface tension forces in the small gap between the front face of the fluid supply nozzle and the oscillating surface. When the fluid supply is stopped, the surface with the tapered apertures is allowed to oscillate for a period of time sufficient for the apertures to draw all the fluid from the oscillating surface and the gap. When not in use, the gap, as well as the oscillating surface and the aperture, remain free of fluid.

The discharge nozzle is preferably made of elastomer material having a cut through its thickness. The cut is normally closed due to the elasticity of the elastomer. The cut opens under slight pressure when fluid is transported from the supply container. This arrangement keeps the fluid in the container hermetically sealed during periods of non-use.

An electronic wave generator with a circuit that can turn the oscillating action on and off sequentially at a very high speed is preferred. The ratio of the "on" period versus the "off" period controls the duty cycle of ejection and, therefore, the ejection mean flow rate. Maximum flow is achieved when the oscillator is continuously "on."

Fluid is preferably supplied to the oscillating surface at a rate that is lower than the maximum ejection rate of the aperture. If the fluid supply exceeds the maximum ejection rate of the apertures, excessive fluid may overflow from the supply side of the oscillating surface. When the fluid used is paint or ink, overflow is undesirable. To prevent overflow, a system to collect liquid overflow may be used. This system includes a ring provided with a slot at its circumference which is connected to a pump. If fluid accidentally escapes from the oscillating surface and reaches the slot, it is drawn and returned to the supply container.

Another method of preventing accidental overflow is provided by an electronic flow control valve. It has been found that as the amount of liquid over the surface increases, the current draw by the piezoelectric element decreases. If the current draw reaches a predetermined level which indicates that an overflow is about to occur, the electronic circuit transmits a signal to the flow control valve to reduce the flow of liquid to the surface. Thereby, overflow is avoided.

DESCRIPTION OF THE PREFERRED EMBODIMENTS

Referring now to FIG. 1, it will be seen that the fluid ejection device 10 of the present invention comprises a vibrating surface 12 having a perimeter area 14 and a center area 16. The perimeter 14 of vibrating surface 12 is affixed to an oscillator 18 which may, for example, be piezoceramic. The center area 16 of vibrating surface 12 is provided with a planar surface 15 through which there are apertures 22. The portion of center 15 having the apertures is in surface tension contact with a fluid film 19 at the back side of planar surface 15 to produce an ejection of fluid droplets 20.

Figure 2:
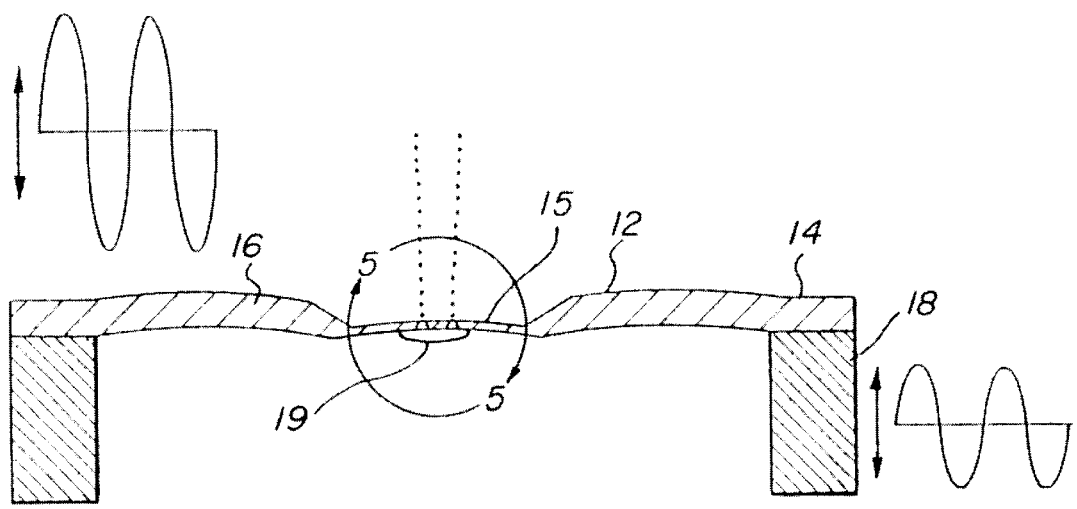
FIG. 2 is the schematic illustration of the present invention of FIG. 1 shown in its oscillating configuration.

The oscillatory motion of the vibrating surface 12 is shown in FIG. 2. It will be seen therein that the perimeter 14 of the vibrating surface 12, by virtue of its contact with the oscillator 18, oscillates in a vertical direction, as viewed in FIG. 2, with an oscillating characteristic shown in the graph at the rightmost portion of FIG. 2. As also seen in FIG. 2, the center 16 of vibrating surface 12 oscillates at the same frequency as the perimeter 14, but with a much larger amplitude, as seen in the graph on the leftmost portion of FIG. 2. The graphs of FIG. 2 are for purposes of illustration and are not necessarily drawn to scale.

Figure 3:
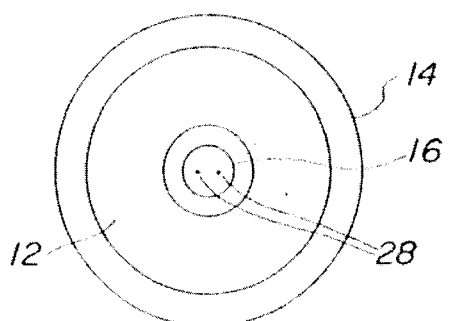
FIG. 3 is a top view of a vibrating surface according to the present invention.
Figure 4:
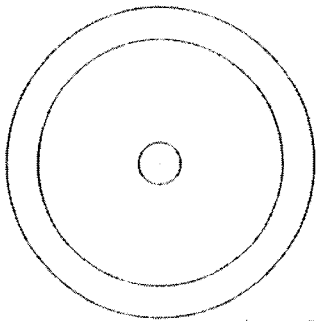
FIG. 4 is a bottom view of a vibrating surface according to the present invention.
Figure 5:
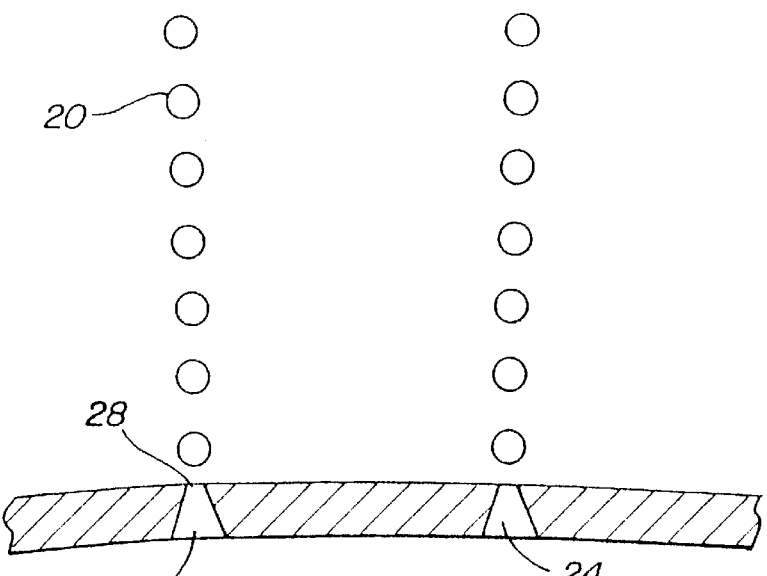
FIG. 5 is an enlarged cross-sectional view of the center area of the membrane shown in FIG. 2 and labelled "5"
Figure 6:
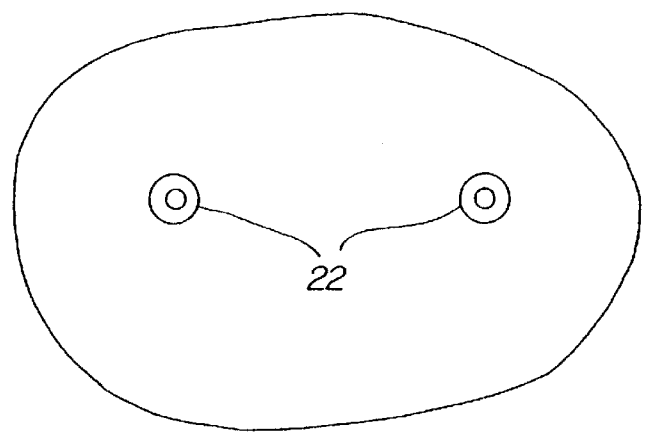
FIG. 6 is an enlarged elevational view of the center area of the vibrating surface of the present invention showing a preferred aperture shape.

The significantly larger oscillation amplitude of the center of the vibrating surface in FIG. 2, as compared to the perimeter, is due primarily to two factors. One is the shape of the vibrating surface 12 and the other is the frequency of oscillation that is selected for activation of the oscillator 18. More specifically, vibrating surface 12 is configured so that its cross-section is reduced toward the center. The vibrating surface configuration may be understood best by referring to FIGS. 2, 3, and 4, which illustrate a preferred embodiment thereof. The apertures 22 in vibrating surface 12 may be understood best by referring to FIGS. 5 and 6. As seen therein, the center portion 15 (FIG. 5) of the vibrating surface 12 is provided with apertures 22, each characterized by a tapered wall 24, forming a large opening 26 on one side of the center portion 15 and a small opening 28 on the opposite side thereof. The thickness of the center portion 15 of the vibrating surface 12 is preferably 0.003-inch. Each aperture 22 is positioned at or near the center of the vibrating surface and is circular in shape with large opening 26 having a radius of 0.006-inch and the small opening 28 thereof having a radius of 0.0025-inch.

The shape of vibrating surface 12 and, in particular, the reduction in cross-section of the vibrating surface between its perimeter 14 (FIG. 3) and its center 16, is selected to provide a significant increase in amplitude of oscillation between the perimeter and the center of vibrating surface 12. This increase in oscillation amplitude has been found to occur at particular frequencies of oscillation of the vibrating surface 12 such as at the second harmonic of the natural oscillating frequency of the vibrating surface. In the preferred embodiment of the present invention, it is desirable to have a damping ratio of at least 10 percent and to provide an amplitude ratio between the center area and the perimeter of the vibrating surface of at least 10, depending upon the voltage applied to the oscillator 18 and its mechanical responsiveness thereto.

When the center of the vibrating surface oscillates with an amplitude which exceeds a preselected threshold, fluid droplets are ejected from aperture 22 (FIG. 1) at the frequency of oscillation of oscillator 18. Thus, by controlling the amplitude of the perimeter oscillation and, thus, the amplitude of the center oscillation so that it is either above or below this threshold ejection level, the ejection of fluid droplets may be readily controlled.

In one embodiment that has been reduced to practice, the oscillation amplitude is 0.0001-inch at the perimeter. The frequency of oscillation is approximately 60,000 Hz, which corresponds to the second modal frequency of the vibrating surface 12. The fluid droplet ejection level, that is, the level above which the amplitude of oscillation of the center 15 of the vibrating surface 12 causes fluid droplets to be ejected therefrom, is approximately 0.0016-inch. The perimeter oscillation is adjusted so that the center oscillation varies in amplitude from cycle to cycle, so that it is just above the ejection level and below the ejection level upon alternate cycles. The actual ejection level threshold, that is, the actual oscillation amplitude of the center of the vibrating surface which causes the ejection of fluid droplets, depends upon the characteristics of the fluid selected, as well as the shape and dimensions of the aperture 22. In the particular preferred embodiment shown herein, the ejection level is achieved using gasoline.

Figures 7, 8:
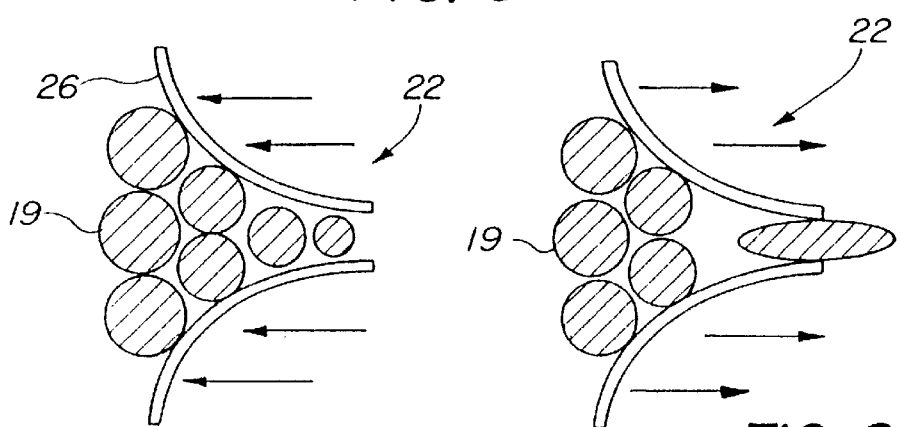
FIG. 7 is a schematic illustration of the fluid characteristic within a tapered aperture during half of an oscillation cycle.
FIG. 8 is a schematic illustration of the fluid characteristic with a tapered aperture during half of an oscillation cycle.

As shown in FIGS. 7 and 8, fluid 19 continuously adheres through solid/fluid surface tension to the large opening 26 of aperture 22. The fluid is compressed in the first half of the oscillation (FIG. 7) when the vibrating surface strokes toward the fluid and decompresses in the second half of the oscillation cycle (FIG. 8) when the vibrating surface strokes away from the fluid. Droplets are ejected each time the amplitude of oscillation of the aperture element 15 (FIG. 5) exceeds the ejection level threshold. The number of droplets and spacing there-between are a function of the frequency of oscillation. In the preferred embodiment hereof, at a 60,000-Hz oscillation frequency, it has been found that when the ejection amplitude is continually above the threshold level, droplets are attached to each other and form a continuous stream. By altering the oscillation amplitude, such as by reducing it below the threshold level every second cycle, the droplets can be separated. This feature is particularly advantageous in fuel injection systems. It will be understood, however, that with selected changes in the shape of the vibrating surface 12, the characteristic of the fluid, and in the shape and dimensions of aperture 22, the selected frequency of operation may vary from that recited herein. Nevertheless, based upon the preferred embodiment disclosed herein, it will now be understood that ejection may be achieved by the present invention and that, in fact, fluid-droplet ejection at frequencies exceeding 60,000 Hz is readily achieved.

Figure 9:
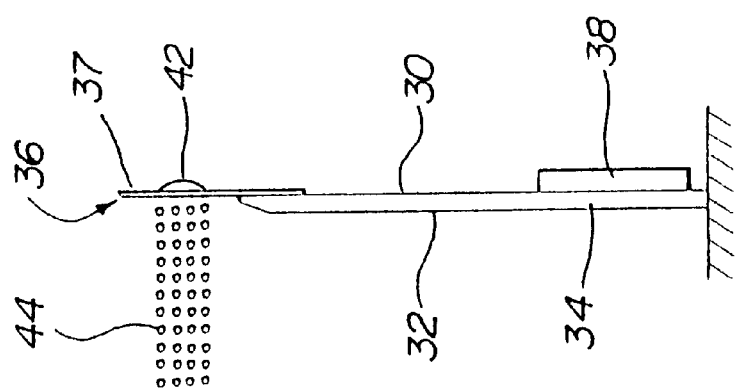
FIG. 9 is a side view of an alternate preferred embodiment of the fluid ejection device according to the present invention.

FIG. 9 illustrates an alternate preferred embodiment of the fluid ejection device 30 of the present invention which comprises a cantilever beam 32 including a base portion 34 and a free end 36. The base portion 34 is affixed to a piezoelectric oscillator 38. The free end 36 of the beam 32 is provided with a planar surface through which there are nine microscopic tapered apertures. Fluid 42 is in contact with the free end 36 through which droplets 44 are ejected.

Figure 11:
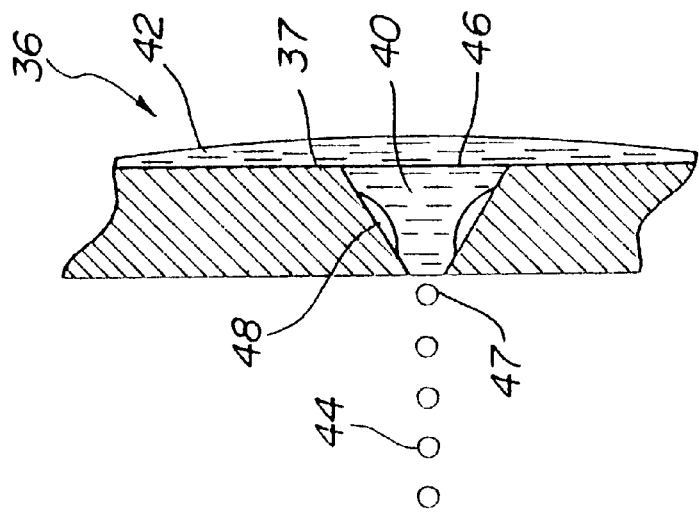
FIG. 11 is an enlarged cross-sectional side view of the free end of the fluid ejection device of FIG. 9.
Figure 10:
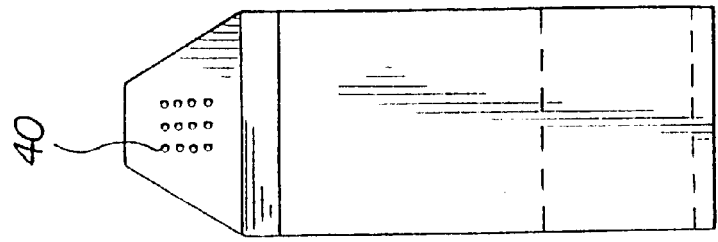
FIG. 10 is a front view of the fluid ejection device of FIG. 9.

FIG. 10 provides a front view of the fluid ejection device 30 and best illustrates the apertures 40. FIG. 11 is an enlarged cross-sectional side view of the fluid ejection device 30 showing the free end 36 in contact with the fluid 42. The large opening 46 of each aperture 40 is in surface tension contact with the fluid 42. The piezoelectric element 38 (FIG. 9) produces high-frequency oscillations at the base end 34 of the beam 32. The planar surface 37 at the free end 36 oscillates at the same frequency as the base 34, but with much greater amplitude. Such oscillation of the free end 36 is due primarily to two factors: the beam 32 is shaped such that its moment of inertia is reduced toward the free end 36; and the induced frequency is substantially the natural frequency of the beam 32.

The oscillation of the planar surface 37 produces cycles of pressure fluctuation at the interface between the fluid 42 and the surface 37 and inside the apertures 40. The pressure fluctuation inside the apertures 40 and, particularly, near the inside wall 48 of each aperture, is significantly more intense as compared to the pressure fluctuation near the planar surface 37. This characteristic is exclusively attributed to the conical cross-sectional geometry of the apertures 40. As a result, fluid cavitation is developed inside each aperture 40 at an oscillation amplitude that is too small to dynamically disturb the fluid 42 near the planar surface 37. The cavitation inside the aperture 40 produces a negative pressure that draws fluid from the planar surface 37 into the large opening 46 of the aperture 40 and ejects a stream of droplets 44 from its small opening 47 to a great distance. The ultrasonic oscillations do not break up or nebulize the fluid 42 at the surface 37, such fluid remaining dynamically at rest during the ejection of fluid 42 within the aperture 40. Ejection continues until all the fluid 42 is drawn from the surface 37 and ejected forwardly as droplets 44. In this preferred embodiment, the diameter of the large opening 46 of the aperture 40 is 0.006" and the diameter of the small opening 47 is 0.0025". The thickness of the planar surface 37 is 0.003" and the oscillation frequency is 50 kHz, which is the third natural frequency of the beam 32.

Figure 12:
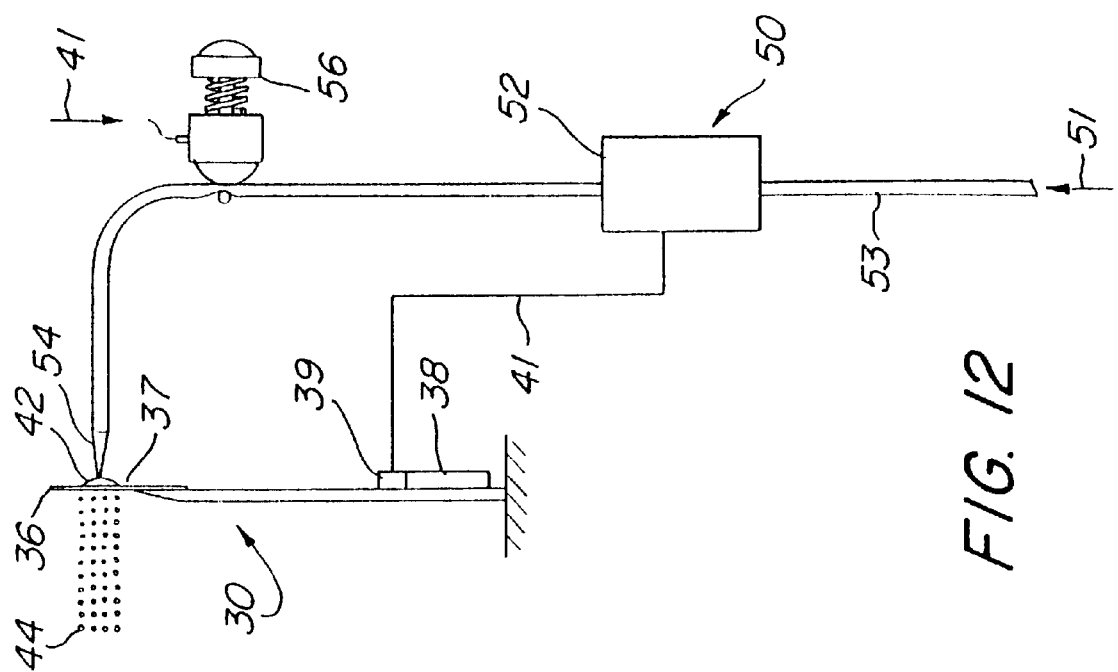
FIG. 12 illustrates the ejector of FIG. 9 provided with a fluid supply system.

Referring now to FIG. 12, the ejector 30 described in the specification with respect to FIGS. 9, 10, and 11 is now provided with a fluid supply system 50 that continuously transports fluid 51 to wet the oscillating surface 37 via a supply tube 53 ending at a supply nozzle 54. The fluid 51 is transported to the surface 37 at a rate which is lower than the maximum ejection rate of the apertures 40 to prevent overflow of fluid 42 from the supply side of the oscillating surface 37. A pinch valve 56 controls delivery of the fluid 51 to the oscillating surface 37. The fluid supply system 50 is connected to an electronic flow control valve 52 which, in the preferred embodiment, is made by ICS sensors. The valve 52 is connected to an electronic circuit that detects the amount of liquid 42 on the oscillating surface 37. In the event of excessive delivery of fluid, the oscillation amplitude decreases and the current draw by the piezo-electric element 38 decreases. A current sensor circuit 39 senses the current draw and transmits an overflow signal 41 to the flow control valve 52 to reduce the delivery rate of liquid 51 to the surface 37 until the amount of fluid returns to a normal level.

Figure 13:
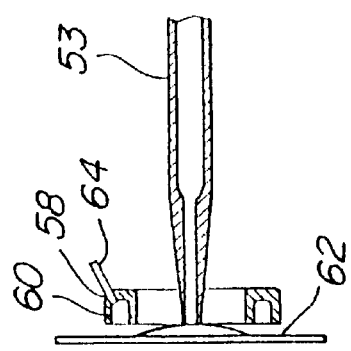
FIG. 13 illustrates an alternative apparatus for preventing accidental overflow in the fluid supply system of FIG. 12.

FIG. 13 illustrates an alternative apparatus for preventing fluid overflow with the fluid supply system 50. An additional ring element 58 including a slot 60 is installed near the oscillating surface 37 such that the slot 60 is positioned a predetermined distance from the boundary 62 of the fluid 42. The preferred ring element 58 is manufactured by Clippard Instruments Laboratory, Inc. of Cincinnati, Ohio and is designated as Model No. 1022. The slot 60 is connected to a suction venturi pump (not shown) through an inlet 64. A suction venturi pump, designated as Part No. 16480, is commercially available from Spraying Systems Co. of Wheaton, Ill. In the event of overflow, the boundary 62 of the fluid 42 expands toward the ring 58 and returns to the supply line 53.

Figure 14:
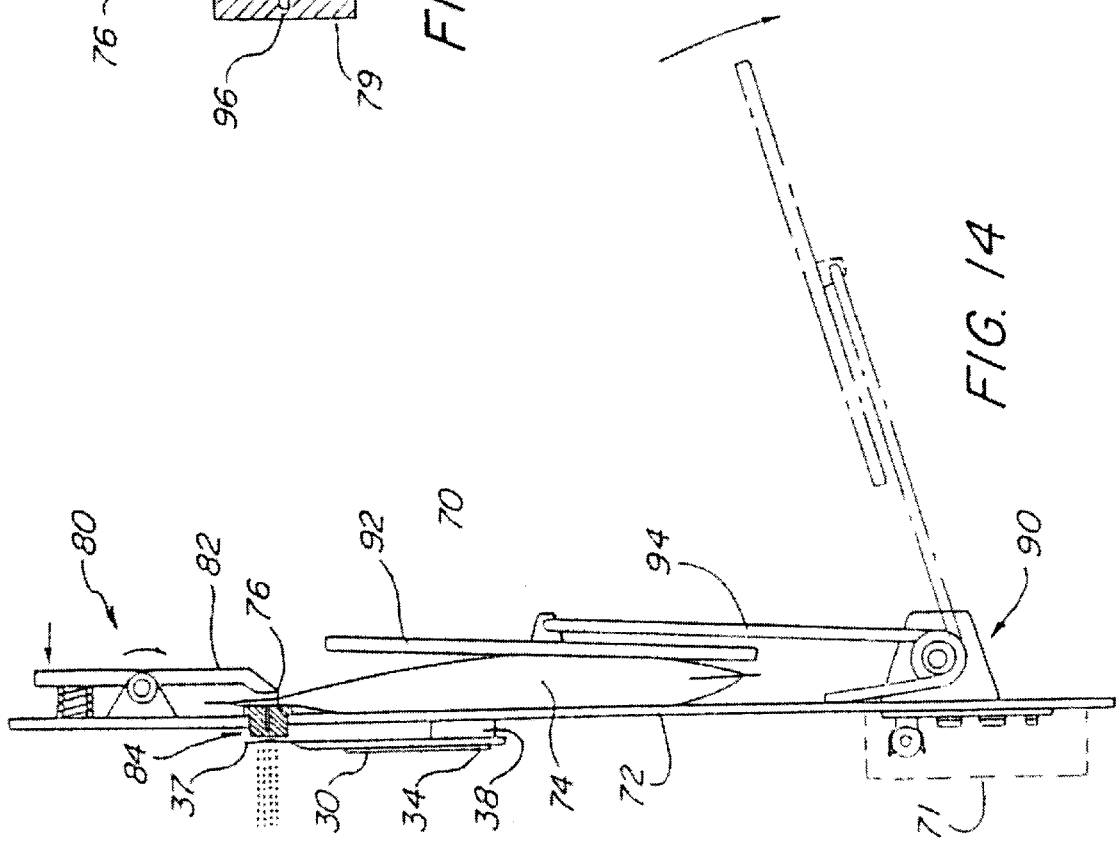
FIG. 14 illustrates the ejector of FIG. 9 provided with an alternative fluid supply system.
Figure 18:
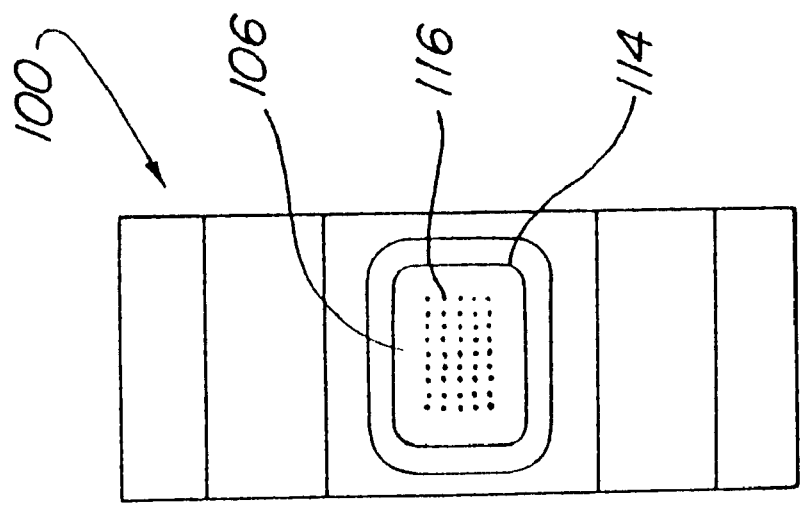
FIG. 18 is a front view of the fluid ejection device of FIG. 17.

FIG. 14 shows the ejection device 30 of FIG. 9, further including an alternative fluid supply system 70 and an electrical wave generator 71 including a battery or external power inlet (not shown) to activate the piezoceramic element. The ejector device 30 is preferably attached to a platform 72 of the supply system 70 at the piezoelectric oscillator 38. The supply system 70 includes a fluid supply container 74 which is preferably made from a flexible, disposable nylon material. A discharge nozzle 76 is affixed at a side wall of the supply container 74 providing fluid communication between fluid in the tube and the ejection device 30. When force is applied to the side of the supply container 74, the fluid inside the supply container 74 is pressurized and forced through the discharge nozzle 76.

The supply system 70 further includes a discharge valve apparatus 80 which is preferably attached to the platform 72. The preferred discharge apparatus 80 includes a spring-loaded plunger 82 acting on the external side wall of the supply container 74 against a rear opening of the discharge nozzle 76 to prevent unwanted discharge of fluid from the supply container 74. When the plunger 82 is released, fluid is discharged toward the oscillating surface 37. Fluid enters into a gap 84 between the nozzle 76 and the surface 37 and is held by surface tension contact. In the preferred embodiment this gap is 0.025".

The alternative fluid supply system 70 additionally provides a means for applying mechanical pressure 90 on the nylon container 74 to force the fluid through the nozzle 76. The pressure-applying means 90 includes a pressure plate 92 pivotally attached to a torsion spring 94 for applying a compressive force on a side wall 75 of the container 74. As shown in FIG. 14, the pressure plate 58 can be rotated clockwise to a released position, facilitating the unloading and loading of fluid supply containers 74. In operation, the pressure plate 92 applies a continuous pressure of approximately 10 psi to the fluid inside the nylon container 74.

Figure 15:
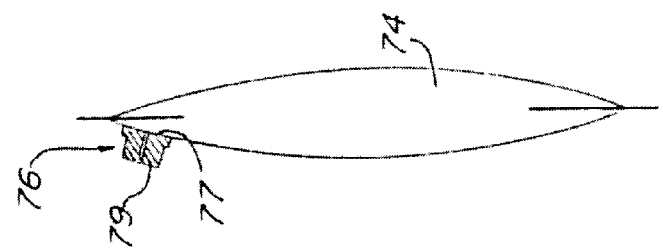
FIG. 15 is an enlarged cross-sectional side view of the fluid supply tube of FIG. 14 including a discharge nozzle attached at a side wall of the supply tube.

FIG. 15 provides an enlarged cross-sectional side view of the supply container 74 including an integrally-formed discharge nozzle 76 attached at a side wall of the container 74. The nozzle includes a rear surface 77 in fluid communication with fluid inside the supply container 74 and a front surface 79 positioned in close proximity to the vibrating free surface 37.

Figure 16:
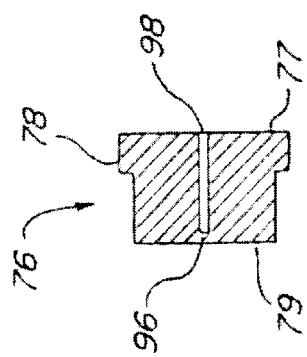
FIG. 16 is an enlarged cross-sectional side view of the discharge nozzle of FIG. 14.

FIG. 16 provides an enlarged cross-sectional side view of the discharge nozzle 76. As can be readily appreciated, a circumferential ridge 78 formed around the discharge nozzle 76 ensures that the gap 84 is maintained at its preferred distance. The nozzle 76 is preferably made of an elastomer material and includes a cut 96 through part of its thickness. The cut 96 is normally closed because of the natural elasticity of the elastomer material. Fluid pressure applied to the rear side of the nozzle opening 98 forces the cut 96 to open and allow passage of liquid to the oscillating surface 37. The discharge nozzle 76 is designed to keep the fluid in the supply tube 76 hermetically sealed when the fluid ejection device 30 is not in use.

Figure 17:
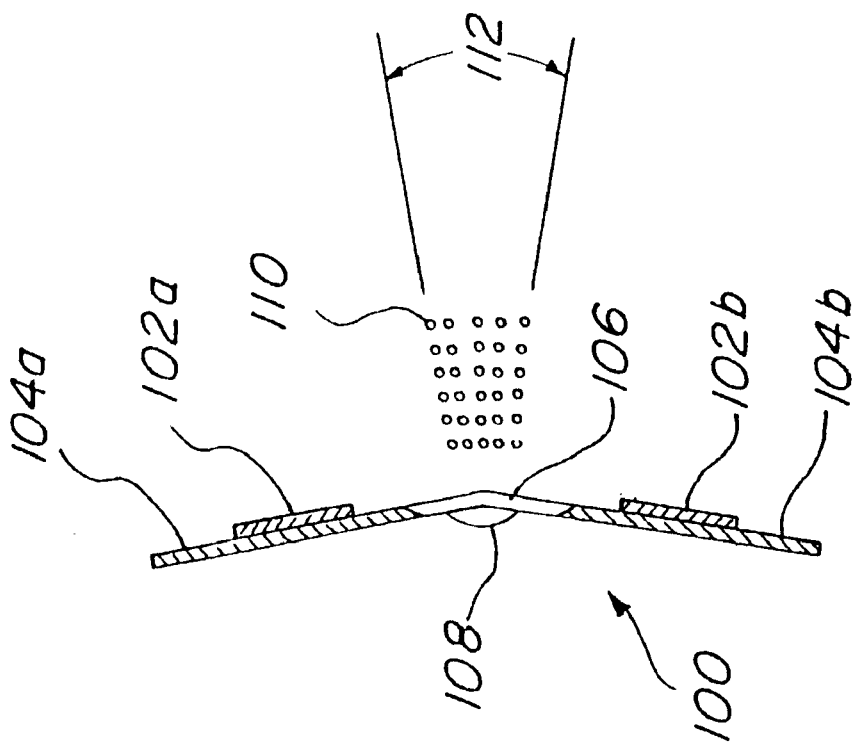
FIG. 17 is a side view of another alternative preferred embodiment of the fluid ejection device according to the present invention.

FIG. 17 illustrates another alternative preferred embodiment of the fluid ejection device wherein the oscillating surface comprises a curved member 100 with two piezoelectric elements 102a, 102b respectively affixed to front surfaces 104a, 104b. The piezoelectric elements 102a, 102b impart oscillations to a thin angled surface 106 located centrally on the curved member 100, causing fluid 108 to be ejected forwardly as a divergent stream of droplets 110. A predetermined curvature characteristic of the angled surface 106 results in a wider distribution of the droplets 110 within an ejection angle 112. FIG. 18 provides a front view of the curved member 100 and further illustrates that the angled surface 106 is bound on its perimeter by a window opening 114. Preferably, the angled surface 106 includes 45 apertures 116 in a 5×9 matrix.

It will now be understood that what has been disclosed herein comprises a novel and highly innovative fluid ejection device readily adapted for use in a variety of applications requiring the ejection of small droplets of fluid in a precisely controlled manner.

Those having skill in the art to which the present invention pertains will now, as a result of the Applicant's teaching herein, perceive various modifications and additions which may be made to the invention. By way of example, the shapes, dimensions, and materials disclosed herein are merely illustrative of a preferred embodiment which has been reduced to practice. However, it will be understood that such shapes, dimensions, and materials are not to be considered limiting of the invention which may be readily provided in other shapes, dimensions, and materials.

What is claimed is:

1. A droplet ejector device comprising:

a vibrating surface having a tapered aperture, said aperture having first and second openings, with said first opening being larger than said second opening;

means for supplying fluid to said vibrating surface to be in surface tension contact with said first opening; and means for vibrating said vibrating surface to eject the fluid supplied to said vibrating surface.

2. The droplet ejector device of claim 1 wherein the tapered aperture is conical in shape.

3. The droplet ejector device of claim 1 wherein said vibrating surface comprises a free end of a cantilevered beam including a base portion, said free end having a lower moment of inertia than said base portion, and wherein said vibrating means comprises an electro-mechanical oscillator attached to said base portion for imparting oscillatory motion thereto at substantially a natural frequency of the cantilevered beam.

4. The droplet ejector of claim 1 wherein said fluid supplying means comprises:

a fluid supply tube for carrying said fluid, including a supply nozzle positioned in close proximity to the free end of said vibrating surface; and a flow control valve attached to the fluid supply tube governing the movement of said fluid through said fluid supply tube.

5. The droplet ejector device of claim 1, further comprising a means for preventing overflow of said liquid in said surface tension contact with said first opening on said vibrating surface.

6. A method for ejecting fluid, the method comprising the steps of:

supplying fluid to a vibrating surface having a tapered aperture with first and second openings, said first opening being larger than said second opening, said fluid being in surface tension contact with said first opening; and oscillating said vibrating surface to eject said fluid drawn into said tapered aperture at said first opening, from said second opening.

7. An ejection device for ejecting fluid on demand, said device comprising:

a vibrating surface having at least one aperture, said aperture having first and second openings wherein said first opening is larger than said second opening;

an oscillator attached to the said vibrating surface for imparting oscillating motion thereto at a selected frequency; and a liquid supply means in fluid communication with said first opening of the aperture in said vibrating surface for supplying fluid to be ejected, said supplied fluid continuously adhering to said first opening through a solid/fluid surface interaction.

8. The ejection device recited in claim 7 wherein said selected frequency is a natural oscillating frequency of said vibrating surface.

9. The ejection device recited in claim 7 wherein said oscillator comprises a piezoelectric material which oscillates in response to an applied oscillating electrical voltage.

10. The ejection device recited in claim 7 wherein said vibrating surface is shaped to provide a ratio of center oscillation amplitude to perimeter amplitude which is at least 10 when the average structural damping ratio of said surface is at least 10 percent and said selected frequency is a harmonic of the natural oscillating frequency of said surface.

11. The ejection device recited in claim 7 wherein said selected frequency is sufficient to compress the fluid inside said tapered aperture in the first half of a cycle of each oscillation and eject fluid in the second half of a cycle of oscillation.

12. The ejection device recited in claim 7 wherein fluid droplets are ejected by said aperture only when the oscillation amplitude of said vibrating surface exceeds a threshold amplitude.

13. A fluid ejection device comprising:

a mechanical member constrained at a portion thereof and free to move at another portion thereof and adapted for vibrating motion at its free portion in response to oscillations;

said mechanical member having a tapered aperture in its free portion, said aperture having first and second openings wherein said first opening is larger than said second opening;

an oscillator for imparting mechanical oscillations to said mechanical member in response to an electrical signal; and a source of fluid in fluid communication with said first opening of said tapered aperture for supplying fluid to said aperture, said fluid continuously adhering to said first opening through a solid/fluid surface interaction.

14. The ejection device recited in claim 13 wherein a frequency and amplitude of oscillation at the free portion of the mechanical member are sufficient to compress the fluid inside the aperture in the first half of an oscillation cycle and create cavitation of fluid in said aperture in the second half of an oscillation cycle.

15. The ejection device recited in claim 13 wherein said fluid source comprises a fuel supply for delivering fuel to said free portion of the said membrane for controlled ejection therefrom.

16. The ejection device recited in claim 15 wherein said tapered aperture receives said fuel and ejects said fuel as droplets at a rate dependent upon said selected frequency.

17. A method for ejecting fluid droplets, said method comprising the steps of:

a. providing a vibrating surface of selected shape having at least one aperture, said aperture having first and second openings wherein said first opening is larger than said second opening;

b. oscillating said surface; and c. supplying fluid in surface tension contact with the first opening of said aperture.

18. The method recited in claim 17 wherein the amplitude and natural oscillating frequency of said vibrating surface are sufficient to compress the fluid in said aperture.

19. In an unpressurized fluid injection system, a fluid droplet ejection device comprising:

a mechanical member contained at a portion thereof and free to move at another portion thereof and adapted for vibrating motion at its free portion in response to oscillations, said mechanical member having a tapered aperture in its free portion, said aperture having first and second openings, said first opening being larger than said second opening;

an oscillator for imparting mechanical oscillations to said mechanical member in response to an electrical signal; and an unpressurized source of fluid in fluid communication with said first opening for supplying fluid to said aperture, said fluid continuously adhering to said first opening through a solid/fluid surface interaction.

20. A method of dispensing a liquid as an atomised spray comprising the steps of maintaining the liquid in contact with a rear surface of a vibratable perforate membrane defining an array of holes, each hole being flared such that the cross-section of each hole narrows in a direction from the rear surface towards a front surface of the membrane, and vibrating the membrane such that droplets of the liquid are dispensed through the flared holes as an atomised spray.

21. A method of dispensing a liquid as an atomised spray comprising the steps of maintaining the liquid in contact with a rear surface of a perforate membrane defining an array of holes, each hole being flared such that the cross-section of each hole narrows in a direction from the rear surface towards a front surface of the membrane, said membrane being stiffened by means of a grid of support elements, and said membrane having a sheet defining the array of holes and having thickened portions constituting the support elements, and vibrating said membrane with the grid of support elements and flared holes such that droplets of the liquid are dispensed through the holes as an atomised spray.

22. A method as claimed in claim 21 wherein the liquid comprises a pharmaceutical product in aqueous solution or suspension.

23. Dispensing apparatus for use in dispensing liquid as an atomised spray comprising a vibratable-perforate membrane defining an array of holes and having a front surface and rear surface, liquid supply means for supplying the liquid in contact with the rear surface, and vibrating means operable to vibrate the membrane relative to the liquid supply means such that droplets of the liquid are dispensed through the holes as an atomised spray, wherein each hole is flared such that the cross-section of each hole narrows in a direction from the rear surface towards the front surface.

24. Dispensing apparatus for use in dispensing liquid as an atomised spray comprising a perforate membrane defining an array of holes and having a front surface and a rear surface, liquid supply means for supplying the liquid in contact with the rear surface, and vibrating means operable to vibrate the membrane such that droplets of the liquid are dispensed through the holes as an atomised spray; wherein each hole is flared such that the cross-section of each hole narrows in a direction from the rear surface towards the front surface, wherein the perforate membrane comprises a sheet defining the array of holes through which liquid is dispensed in use and support means supporting the sheet, and wherein said support means comprises a grid of support elements.

25. Dispensing apparatus as claimed in claim 24 wherein the support elements are formed integrally with the sheet and comprise thickened portions thereof.

26. Dispensing apparatus as claimed in claim 24 wherein the perforate membrane comprises an electroformed metal sheet.

27. Apparatus as claimed in claim 24 wherein each hole is defined by a generally tubular surface extending through the membrane, the tubular surface comprising a substantially cylindrical portion intersecting substantially at right angles with the front surface of the membrane and a flared portion merging smoothly with the cylindrical portion and increasing in aperture at a progressively increasing rate with respect to distance towards the rear surface so as to merge smoothly and continuously with the rear surface.

28. A method of dispensing a liquid as an atomised spray comprising the steps of maintaining the liquid in contact with a rear surface of a vibratable perforate membrane having at least one hole, the hole being flared such that the cross-section of the hole narrows in a direction from the rear surface towards a front surface of the membrane, and vibrating the membrane such that droplets of the liquid-are dispensed through the flared hole as an atomised spray.

29. Dispensing apparatus for use in dispensing liquid as an atomised spray comprising a vibratable perforate membrane having at least one hole and having a front surface and rear surface, liquid supply means for supplying the liquid to the rear surface, and vibrating means operable to vibrate the membrane relative to the liquid supply means such that droplets of the liquid are dispensed through the hole as an atomised spray, wherein the hole is flared such that the cross-section of the hole narrows in a direction from the rear surface towards the front surface.

* * * * *